US012346102B2

(12) United States Patent
Cussonneau et al.

(10) Patent No.: US 12,346,102 B2
(45) Date of Patent: Jul. 1, 2025

(54) COMBINED METHOD FOR DETECTING ANOMALIES IN A WATER DISTRIBUTION SYSTEM

(71) Applicant: SUEZ INTERNATIONAL, Paris la Défense (FR)

(72) Inventors: Guillaume Cussonneau, Paris (FR); Pierre-Antoine Jarrige, Montesson (FR); Abel Dembele, Villeurbanne (FR); Francis Campan, Antony (FR)

(73) Assignee: SUEZ INTERNATIONAL, Paris, la Defense (FR)

( * ) Notice: Subject to any disclaimer, the term of this patent is extended or adjusted under 35 U.S.C. 154(b) by 890 days.

(21) Appl. No.: 15/737,710

(22) PCT Filed: Jun. 29, 2016

(86) PCT No.: PCT/EP2016/065213
§ 371 (c)(1),
(2) Date: Dec. 18, 2017

(87) PCT Pub. No.: WO2017/001523
PCT Pub. Date: Jan. 5, 2017

(65) Prior Publication Data
US 2019/0004484 A1 Jan. 3, 2019

(30) Foreign Application Priority Data

Jun. 29, 2015 (EP) ...................................... 15306029
Sep. 30, 2015 (EP) ...................................... 15306546

(51) Int. Cl.
*G05B 23/02* (2006.01)
*G01N 33/18* (2006.01)
(Continued)

(52) U.S. Cl.
CPC ..... *G05B 23/0259* (2013.01); *G05B 13/0265* (2013.01); *G05B 13/04* (2013.01);
(Continued)

(58) Field of Classification Search
CPC .... G05B 23/0259; G05B 17/02; G05B 13/04; G05B 13/0265; G05B 13/041;
(Continued)

(56) References Cited

U.S. PATENT DOCUMENTS 8,635,051 B1 * 1/2014 Wu ........................ G06N 3/126
703/9
2013/0211797 A1 * 8/2013 Scolnicov .............. G06Q 50/06
703/2

(Continued)

FOREIGN PATENT DOCUMENTS

CL    2217-2009      1/2011
CN    102201065 A    9/2011
(Continued)

OTHER PUBLICATIONS

Chinese office Action with English translation issued in Chinese Patent Application No. 201680049486.5 mailed Apr. 20, 2020.
(Continued)

*Primary Examiner* — Michael W Ayers
*Assistant Examiner* — Beatriz Ramirez Bravo
(74) *Attorney, Agent, or Firm* — BakerHostetler

(57) ABSTRACT

A method for the detection of anomalies in a networked water distribution system is provided. It improves detection methods based on an iterative modification of control variables of the network, by determining a reduced set of entities of the water distribution network on which control variables should be iteratively modifier. The invention increases the computing costs, and the reliability of such methods of detecting anomalies in a water distribution system.

17 Claims, 8 Drawing Sheets

(51) Int. Cl.
  *G05B 13/02* (2006.01)
  *G05B 13/04* (2006.01)
  *G05B 17/02* (2006.01)
  *G06F 30/20* (2020.01)
  *G06F 111/10* (2020.01)
  *G06N 7/01* (2023.01)
  *G06N 20/00* (2019.01)
  *G06Q 50/06* (2024.01)

(52) U.S. Cl.
  CPC ......... *G05B 13/041* (2013.01); *G05B 13/048* (2013.01); *G05B 17/02* (2013.01); *G06F 30/20* (2020.01); *G06N 7/01* (2023.01); *G06N 20/00* (2019.01); *G01N 33/18* (2013.01); *G06F 2111/10* (2020.01); *G06Q 50/06* (2013.01)

(58) Field of Classification Search
  CPC ... G05B 13/048; G06F 30/20; G06F 2111/10; G06N 20/00; G06N 7/005; G01N 33/18; G06Q 50/06
  USPC .......................................................... 706/12
  See application file for complete search history.

(56) References Cited

U.S. PATENT DOCUMENTS

2014/0052421 A1\* 2/2014 Allen ..................... G05B 17/02
  703/2
2014/0163916 A1\* 6/2014 Ba .......................... G06Q 50/06
  702/100

FOREIGN PATENT DOCUMENTS

| CN | 102681442 A | 9/2012 | |
|---|---|---|---|
| EP | 3 112 959 A1 | 1/2017 | |
| WO | WO-2010131001 A1 \* | 11/2010 | ............ G06Q 50/06 |
| WO | 2013/026731 A1 | 2/2013 | |

OTHER PUBLICATIONS

O. Piller et al., "Dual Calibration for Coupled Flow and Transport Models of Water Distribution Systems," Water Distribution Systems Analysis WDSA Dec. 2010, pp. 722-731.

Piller, "Modeling the behavior of a network - Hydraulic analysis and sampling procedures for parameter estimation" Applied Mathematics thesis from the University of Bordeaux (PRES), 288 pages, Talence, France, Feb. 3, 1995.

\* cited by examiner

COMBINED METHOD FOR DETECTING ANOMALIES IN A WATER DISTRIBUTION SYSTEM

CROSS-REFERENCE TO RELATED APPLICATIONS

This application is a National Stage of International patent application PCT/EP2016/065213, filed on Jun. 29, 2016, which claims priority to foreign European patent application Nos. EP 15306029.8, filed on Jun. 29, 2015 and EP 15306546.1, filed on Sep. 30, 2015, the disclosures of which are incorporated by reference in their entirety.

FIELD OF THE INVENTION

The present invention relates to the detection of anomalies in a water distribution system. More specifically, it relates to the detection of anomalies with the combined use of statistics and a hydraulic model of the water distribution system.

BACKGROUND PRIOR ART

A system for distributing drinkable water is notably made of pipes between a water head and consumers, along with control devices such as valves and pumps. Such system can be subject to numerous anomalies. Anomalies belong to a plurality of types. Hydraulic anomalies comprise leaks, abnormal variation of pressure, fast drop of the water level of a storage tank, incoherent mass balance of storage. Operation anomalies define an element in the system which is in an incorrect state, for example a valve in an opening state different from the one stored in the information system. These anomalies, especially leaks, can dramatically reduce the performance of the water distribution system. For example, leaks in the pipes are the cause of a loss of a significant part of the water between water head and consumers, and can make structural damages. The detection and correction of anomalies in a water distribution system is therefore a permanent concern of the operators of such systems in order to mitigate the economic cost of water loss and damages. Moreover, the detection of leaks in a water distribution system is a key objective for limiting the global water consumption and waste, which is of particular interest in regions subject to water stress, and in view of promoting sustainable development.

The detection of leaks in a water distribution system is historically performed through human inspection. Human inspection generally consists in sending human operators to inspect pipes of the system and identify leaks and other anomalies. This detection can for example be aided using audio sensors, which detect noise due to a leak. However, the typically large size of water distribution systems renders human detection of leaks and anomalies very difficult. For example, the water distribution system of a large city comprises thousands of km of pipes. It is therefore impossible to inspect all pipes frequently at a reasonable cost.

The use of one or more sensors contributes to a solution to the issue of detecting anomalies in a water distribution system. Sensors can notably be used for automatically detecting abnormal changes in the behavior of the system, therefore human operators can be sent to those nodes/arcs of the system wherein abnormal behavior was detected. However, sensor-based detection methods of anomalies have disadvantages as well. They can generate a high number of false positive (alarms for events which are not actual anomalies), and lead to numerous useless and costly human interventions. They can also properly detect anomalies but with imprecise localization, due to the large scale of a typical water distribution system. Otherwise, deploy a high density of sensors in the system could help in locating anomalies more precisely, but it is too costly.

European patent application no EP 15306029.8 filed by the same applicant as the applicant of the instant application discloses methods for detecting anomalies in a water distribution system. A method disclosed in this prior application uses a predicted set of values of parameters of entities of the water distribution system, modeled as a network, for example water velocity and water pressure at different times, according to an hydraulic model of the water distribution system, and values of control parameters of the network, for example the length, roughness of pipes, a prediction of consumption of the users of the network, etc . . . . Said method consists in performing successive iterations of the calculation of predicted values, comparing these values to observations from sensors, and according to the differences between predictions and observations, adjusting the values of parameters, then using method to detect an anomaly according to the values of parameters. This method permits an accurate determination of the values of control parameters of the network that best match the observations from sensors. Certain values of control parameters are representative of anomalies in the network. For example, the prediction of an excessive consumption of water may be representative of a leak in the water distribution system. Machine learning algorithms, trained on exemplary cases of anomalies in a water network, are then able to identify an anomaly according to values of control parameters which are obtained after several occurrences of calculation of predicted values, through the iterative process.

This method has many advantages. It provides an automatic, fast and reliable method for detecting anomalies in a water distribution system, which allows fixing anomalies in the system much faster than using traditional human inspections. Over successive iterations, the modifications to bring to control parameters are identified more and more accurately. This method is efficient for identifying and localizing anomalies in a water distribution system after successive iterations. Moreover, the use of the hydraulic model of the water distribution system allows the operator of a network to localize an anomaly even in an entity of the network which is not equipped with sensors.

However, the large number of parameters that have an impact on the hydraulic model, and the large number of iterations necessary to obtain a satisfactory solution may render the method complex on large water distribution systems. This mitigates the ability of the operator of a water distribution system to identify and fix anomalies in the water distribution system quickly.

There is therefore a need for a method for diminishing the time to detection reported to operator and improve the relevance of the results in terms of identification and localization. For instance time to detection is reduced with optimization of the number of iterations of calculation of control parameters of a water distribution system network that are necessary to achieve a reliable detection of anomalies in the water distribution system.

SUMMARY OF THE INVENTION

To this effect, the invention discloses a method for detecting anomalies in a water distribution system composed of a network of nodes, said method comprising: parametrizing a hydraulic model of the water distribution system with a set of values of control variables characterizing the network and its output at the nodes; using sensors on the network to acquire observations of a subset of state variables at first time references; identifying at least one target entity where to change the values of control variables based on at least said observations; changing the set of values of control variables using a stepwise adjustment of the control variables and a break criterion based on residue values of the state variables; performing a classification of at least one entity of the network in a state according to the set of control variables.

Advantageously, the method further comprises identifying at least one control variable to change based on at least said observations.

This permits an additional reduction of the computing load of the method, by reducing the number of control variables to modify.

Advantageously, identifying at least one target entity where to change the values of control variables based on at least said observations comprises: using the hydraulic model to calculate predicted values of a set of state variables characterizing at least a water velocity and pressure at the nodes, said predicted values being associated to second time references; computing residue values of the subset of the state variables as a difference between predicted values and observations at the second time references; performing a statistical analysis of residue values at an entity of the network at a selection of the time references; classifying the entities of the network based on rules applied to the output of the statistical analysis.

This permits an efficient pre-detection of the at least one target entity, using historical values.

Advantageously, said at least one target entity is identified by being classified in an abnormal state based on the comparison of residue values and a predefined threshold.

This permits an efficient selection of the at least one target entities, by focusing on the entities which have the higher chances of being in an abnormal state.

Advantageously, identifying at least one target entity where to change the values of control variables based on at least said observations comprises: performing a number of tests on observations using a combination of rules; classifying the entities of the network based on the combination of rules on observations.

This permits a simple, yet robust classification of entities without the need to use a hydraulic model.

Advantageously, said at least one target entity is identified by being classified in an abnormal state based on the combination of rules on observations.

This permits a simple, yet robust identification of the at least one target entity.

Advantageously, identifying at least one target entity where to change the values of control variables based on at least said observations comprises: performing a number of tests on statistical deviations of observations using a combination of rules; classifying the entities of the network based on the combination of rules on observations.

This permits a simple, yet robust classification of entities without the need to use a hydraulic model.

Advantageously, said at least one target entity is identified by being classified in an abnormal state based on the combination of rules on statistical deviations of observations.

This permits a simple, yet robust identification of the at least one target entity.

Advantageously, identifying at least one target entity where to change the values of control variables based on at least said observations comprises identifying an arc of the network wherein a value of an observation of water speed exceeds a threshold at a target entity.

This permits a very simple and straightforward identification of the at least one target entity.

Advantageously, the set of values of control variables is performed for at least one event type, and the control variables to modify are based on said at least one event type.

This permits to improve the robustness of the detection and diminish the computing load of the method. Indeed, a reduced number of control variables are modified, which have a higher chance to be linked to an event which occurred in the network.

Advantageously, a plurality of event types is tested, and one instance of changing the set of values of control variables is performed for each event type.

This permits to test in the same time a plurality of different event types.

Advantageously, at least changing the set of values of control variables is performed for at least one event type chosen using classification of the entities of the network based on rules applied to the output of the statistical analysis.

This permits to reduce the computing load of changing the set of values of control variables, by determining more specifically the control variables to change, in accordance to statistical analysis.

Advantageously, the method comprises: detecting an anomaly based on the output of identifying at least one target entity where to change the values of control variables based on at least said observations; if no anomaly is detected, enriching a database of normal states of the entities; if an anomaly is detected: changing the set of values of control variables using a stepwise adjustment of the control variables and a break criterion based on residue values of the state variables; performing the second classification of at least one entity of the network in a state according to the set of control variables.

This permits to reduce the computing load of the method, by launching the iterative adjustment of control variables only if an anomaly is detected based on the observations, and improve the further executions of the method by enriching a database of normal states.

Advantageously, changing the set of values of control variables using a stepwise adjustment of the control variables and a break criterion based on residue values of the state variables comprises: A) changing the set of values of the control variables; B) using the hydraulic model to calculate predicted values of a set of state variables characterizing at least water velocity and pressure at the nodes at the time references; C) computing residue values of the set of state variables as a difference between predicted values and observations at the time references; D) if said differences satisfy a break criterion, going to step F); E) if not, changing the set of values of the control variables (350) and going back to step B); F) if said differences do not satisfy a refinement criterion (360), selecting a subset of the network (370) where to calculate predicted values, going back to step B.

This permits a progressive adjustment of the values of control variables until their values are reliable enough to detect events on the network.

Advantageously, the refinement criterion comprises the calculation of values of one of a least square and a Bayesian objective function, and the selection and modification of control variables is determined by a Levenberg-Marquardt algorithm.

Using a Bayesian objective function permits to calibrate the relative confidence of the measurements and modified values of control and state variables. Using Levenberg-Marquadt algorithm permits to have good convergence and stability qualities.

Advantageously, performing a classification of at least one entity of the network in a state according to the set of control variables is performed by a previously trained machine learning algorithm.

This permits to have rules of classification optimized for a given water distribution system, whose reliability increases over time.

Advantageously, the control variables comprise scalar variables characterizing the topology and the topography of the network, and time-based variables characterizing the inputs and outputs of the network having at least one value at each time reference.

This permits to increase the number of possible events detected by the method.

Advantageously, changing the set of values of the control variables comprises modifying at least one of: the values of a subset of the time-based control variables; the values of a subset of the scalar control variables calculated during a phase of modeling of the network.

This permits to take full advantage of the availability of scalar and time-based control variables.

Advantageously, modifying the values of a subset of the time-based control variables comprises modifying the values of the time-based control variables representative of water consumption.

This permits to detect events which are detected by an abnormal increase of water consumption, for example leaks.

Advantageously, state variables further characterize pressure.

This permits to have a more complete and efficient modeling of the temporal evolution of the physical parameters of the water distribution system.

The invention also discloses a system for detecting anomalies in a water distribution system composed of a network of nodes, said system comprising: sensors of at least water velocity and pressure at a subset of nodes of the network; a computing device comprising a processor; communication links between sensors and the computing device; a storage media; wherein the computing device is configured to: retrieve an initial set of values of control variables characterizing the network and its output at the nodes from the storage media and using it to parametrize a hydraulic model of the water distribution system; use communication links between sensors on the network to acquire observations of a subset of the state variables, said observations having time references; executing one of the method disclosed above.

The invention also discloses a computer program product, stored on a non-transitory computer-readable medium, for detecting anomalies in a water distribution system composed of a network of nodes, said computer program product comprising code instructions for executing one of the methods disclosed above.

The invention increases the robustness and reduces the computing cost of a method of detection of anomalies in a water distribution system based on a stepwise adjustment of control parameters.

The invention permits a precise detection of anomalies on any entity of a water distribution system, even if such entity is not equipped with sensors.

The methods of the invention are able to detect several types of anomalies in a water distribution system.

The precision of the detection of anomalies of a method of the invention increases with the number of uses of the method.

BRIEF DESCRIPTION OF THE DRAWINGS

The invention will be better understood and its various characteristics and advantages will emerge from the following description of a number of exemplary embodiments and its appended figures in which.

DETAILED DESCRIPTION OF THE INVENTION

In this specification, the invention will be described by way of examples related to the detection of leaks, and the detection of abnormal concentration of chlorine. However, the invention is not restricted to these examples and can be applied to the detection of any anomaly in a water distribution system.

Figure 1:
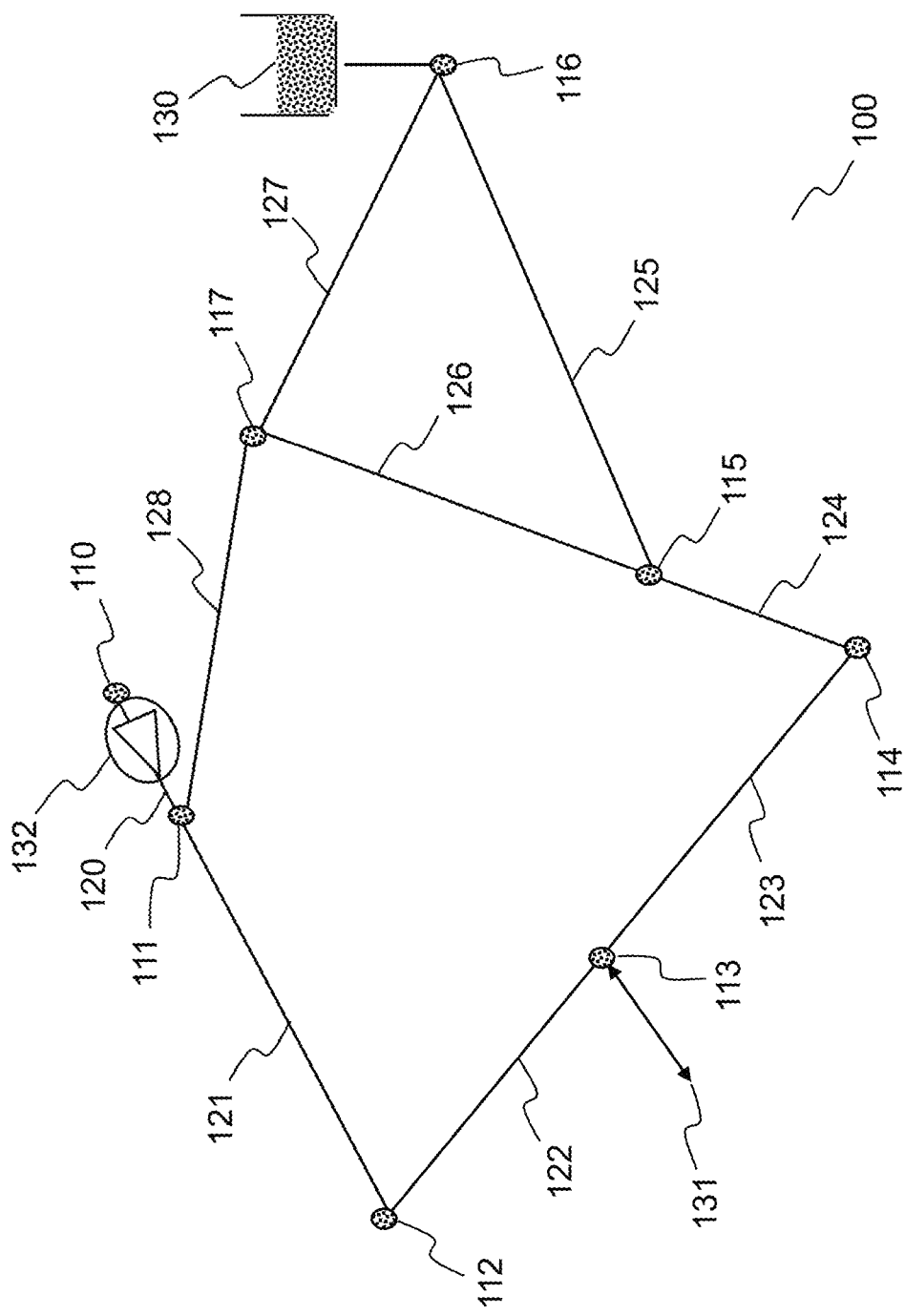
FIG. 1 displays an example of a water distribution system organized in network in the prior art.

FIG. 1 displays an example of a water distribution system organized in a network according to the prior art.

The network 100 displayed on FIG. 1 is organized as a network and comprises a plurality of nodes 110, 111, 112, 113, 114, 115, 116 and 117, and a plurality of arcs 120, 121, 122, 123, 124, 125, 126, 127 and 128. The nodes typically represent the connections with water sources or water reservoirs, for example the reservoir 130 at node 116, the connections with the user of the water distribution system, for example consumption 131 at node 113 and the connections between the arcs. The arcs typically represent pipes between the nodes. The network can be equipped with equipments such as valves and pumps. A pump 132 is for example present on the arc 120. More generally, a node can be a junction between two or three pipes, a point at which inputs or outputs of the network are found, for example a point where a user consumes water, or a point at which water is injected in the network. A node can also represent a sub-network, for example a neighborhood grouped under a single node.

Physical parameters related to water notably comprise by way of example velocity, pressure, flow rate, level in storage (reservoir and tank), temperature, etc . . . . Further parameters can be added according to detection needs and/or the evolution of sensors. The evolution of these parameters over time depends on the characteristics of the water distribution system, the inputs and outputs at the nodes, and the state of the any equipment in the system.

The attributes of the water distribution system notably comprise:
 the topology of the network (i.e. the graph with arcs and nodes);
 the topography of the network (i.e. the elevation of the nodes); the properties of the pipes such as length, diameter, material, roughness, singularities, minor loss coefficients . . . );
 the properties of each equipment of the network (for example pump characteristics, valve diameter, friction coefficient, operating setpoint, . . . ).

The hydraulic model of a drinking water network comprises this set of information.

The inputs and outputs at the nodes are defined by the consumptions or injections of water at every node of the graph. They typically represent the individual consumptions of the users of the water distribution system, and the injection of water from water inlet into the system.

The status of equipment, such as valves or pumps, comprises the operating states and setpoints of these devices.

In this description, the characteristics of the water distribution system, inputs and outputs at the nodes and states of the devices will be referred to as "control variables" of the water distribution system, while the physical parameters at the nodes and arcs will be referred to as "state variables" of the water distribution system. Control variables comprise for example water consumption at the nodes, expressed for example in $m^3/d$, roughness and friction of the pipes, as well as the state of pumps or actuators, . . . . State variables comprise velocity and pressure at the different arcs and nodes. According to the target application, state variables may also comprise levels of water in water tanks and reservoirs, Residual Chlorine Concentration (RCC), etc. The values of state variables vary with time. The values of some control variables, for example those related to the topology or the topography of the network, remain constant, while the values of some control variables, for example those related to the inputs and outputs of the network and to the states of the devices, vary over time. Meanwhile, an entity refers to the whole network, or a subset of a network composed of nodes, arcs and equipments, a single node, a single arc or an equipment of the network which is characterized by characteristics that have an impact on the behavior of the water distribution system.

A description of the initial value of state variables and a prediction (time series) of the values of the control variables, notably the consumptions at nodes of the network, allow a prediction of the values of state variables over time. This prediction is generally performed by computing successive values of the state variables with a fixed or variable time step. This prediction is called resolution of the direct problem.

Some entities of the network are equipped with sensors measuring physical parameters, typically velocity or pressure. These sensors allow obtaining time series of state variables.

Methods are known for computing the values of control variables that define the goodness-of-fit of the system beside the observations of state variables. These methods are generally called inverse problem solving and are notably disclosed by Piller, O. (1995): Modeling the behavior of a network—Hydraulic analysis and sampling procedures for parameter estimation. Applied Mathematics thesis from the University of Bordeaux (PRES), 288 pages, Talence, France, presented on the 3 Feb. 1995 and Piller, O., Gilbert, D. and Van Zyl, J. E. (2010): Dual Calibration for Coupled Flow and Transport Models of Water Distribution Systems. Water Distribution Systems Analysis WDSA 2010, ASCE, Tucson, 722-731, December 2010, U.S. Pat. No. 8,635,051. Solving an inverse problem generally consists in successive iterations of a loop comprising modifying values of control variables, predicting values of state variables according to control variables, in order to minimize a mathematical function that is representative of the differences between prediction and observations of state variables. These techniques allow a determination, for example of the characteristics of an entity of the network (e.g. a head loss in a valve, a roughness of a pipe . . . ) or water consumption that best matches the observations of state variables.

In this application an entity is a general term to designate a node, an arc, equipment, a subset of the network or the whole network. Thus classifying an entity in an abnormal state may consist in identifying an anomaly of a node, an arc, an equipment, a subset of the network, etc . . . .

Figure 2:
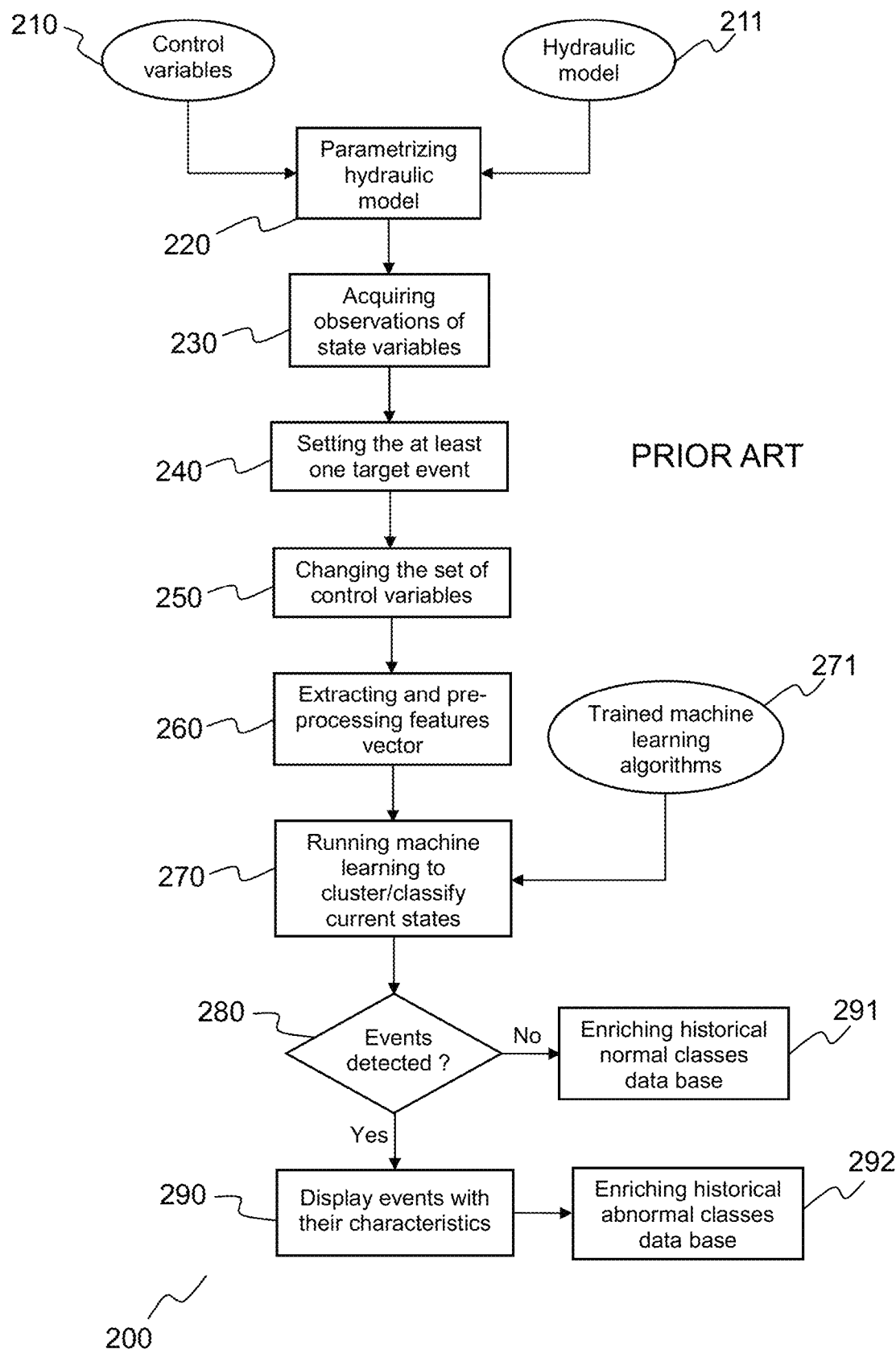
FIG. 2 displays an example of method for detecting anomalies in a water distribution system in a number of embodiments of the invention, using a stepwise iterative adjustment of properties and control variables of a hydraulic model combined to a machine learning for identifying the anomaly in the prior art.

FIG. 2 displays an example of a method for detecting anomalies in a water distribution system in the prior art, using a stepwise iterative adjustment of properties and control variables of a hydraulic model and machine learning for identifying the anomaly.

The method 200 comprises a first step 220 for defining parameters of a hydraulic model 211 using a set of control variables 210. The nature of the hydraulic model and control variables has been presented in relation to FIG. 1. The hydraulic model can notably be configured with control variables characterizing the structure of the network and control variables characterizing a prediction of the inputs and outputs of the network at nodes over a set of time references, notably a prediction of water consumption in the network.

In a preferred embodiment, the values of the control variables related to the structure of the network (e.g. the diameter and roughness of the pipes, characteristics of equipments, etc . . . ) have been calibrated after the creation of the hydraulic model. Indeed, theoretical values defined during the modeling of the network do not always match real values. In order to obtain more accurate values of control variables related to the structure of the network, a calibration step may consist in adjusting the values of these control variables in order to provide the best prediction of the behavior of the network. Typically, this adjustment may consist in:
 performing observations of the inputs, outputs and a subset of the state variables of the network for a certain duration;

configuring the hydraulic model of the network with values of the control variables related to the inputs, outputs and structure of the network;

calculating predicted values of the state variables of the network according to the hydraulic model;

calculating a difference between observed and predicted values of the state variables of the network, and modifying the values of the control variables of the network using an optimization algorithm in order to minimize the distance between observed and predicted values of the state variables of the network.

On the other hand, control variables related to the input and output of the network can be obtained for example using observations of the past inputs and outputs. For example, the values of control variables characterizing water consumption at different nodes can be calculated using historical metered data of water consumption.

The method 200 further comprises a step 230 of using sensors to acquire observations of a subset of state variables, said observations having first time references. A state variable is a timed value of a physical parameter at an entity of the network. State variable often relate to physical values at a node of the network (for example, pressure or concentration of chlorine at a node of the network). They may also relate to a physical value at an arc of the network, for example water speed in a pipe. Parts of prior art methods and the invention rely on a comparison of observations and predictions of state variables. Observations of state variables are only possible if an adequate sensor is present. For example, an observation of pressure at a node of the network can be performed only if a sensor of pressure is present at this node. On the other hand, it is possible to calculate predicted values of state variables at nodes or other entities which are not equipped with sensors, using a hydraulic model. The first time references are associated to each sensor, which is able to produce measurements at different times/rates. According to various embodiments of the invention, the first time references of each sensor may be synchronized, or each sensor may have its own time references. In both cases, execution of the next steps of the method of the invention will be the same.

As stated in relation to FIG. 1, a water distribution system is typically equipped with sensors. These sensors measure physical parameters such as velocity, flow rate, pressure, etc. at the nodes or the arcs of the network, said physical parameters at a node or an arc being state variables of the network. For practical reasons of cost, maintenance and easiness of operation, all nodes and arcs are not equipped with sensors, and those equipped with sensors are usually not equipped with a sensor for each physical parameter. The number and distribution of sensors can be chosen in accordance with the definition of sectors of the water distribution system. The acquisition of observations can be performed remotely. For example, the sensors which are deployed along the network can send the values of state variables to a remote platform through various telecom means, usually wireless links.

The values of state variables vary over time, each value has a time reference that represents the time at which the value has been measured. In an embodiment of the invention, values of state variables are acquired using a predefined time period and sent regularly, possibly but not necessarily, using another period. For example, values of the state variables for which a sensor is present can be acquired and sent every two minutes, 5 minutes, 15 minutes or every hour each 24 hours. In a preferred embodiment of the invention, sensors are synchronized in order to acquire measurements simultaneously. This allows the remote platform to acquire observations of the values of the subset of state variables for which a sensor is available at each time reference. Values can be sent immediately after being measured. They can also be stored locally at transmission device level, and then sent at regular intervals, for example by sending all values that have been captured during 15 minutes, 1 h or any other interval.

The method 200 further comprises a step 240 of setting the at least one target. The step aims at defining targeted events which can be for instance an abnormal variation of pressure, the detection of a valve in a false opening state. These targeted events will be then those to be sought in the following steps of the method, for various entities (whole network, subset of the network . . . ). As explained with reference to FIG. 3, a set of parameters is defined for each type of targeted event at a step 310.

The method 200 further comprises a step 250 of identification of parameters. In a number of embodiments of the invention, the parameters are set for targeted events. In cases wherein a plurality of events are targeted, a step 250 of identifying is executed for each target event, either one after the other, or in parallel. An example of method for identifying parameters in one instance is provided below, with reference to FIG. 3. Various methods exist for determining target events. In a number of embodiments of the invention, events are picked up in a predefined list. In other embodiments one event is selected for a specific application. For example, only a "leak" event may be selected. In yet other embodiments of the invention an operator selects the events it is interested in a list of all possible events. In yet other embodiments of the invention, events that are detectable according to the sensors present in the network are selected. In other embodiments of the invention, no particular event is searched. Thus, a predefined set of parameters can be selected.

Figure 3:
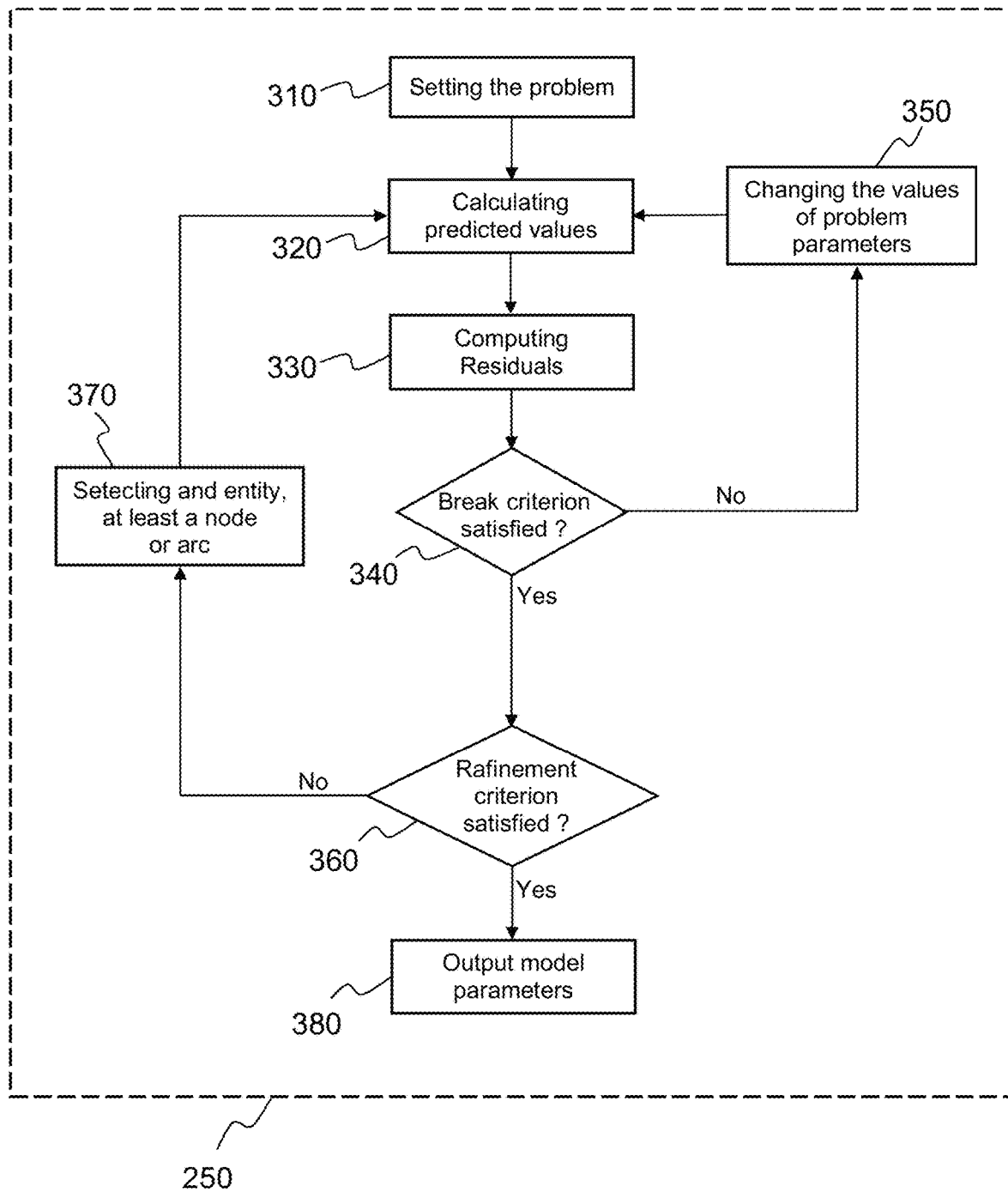
FIG. 3 displays an example of a method for identifying parameters for a target event in the prior art.

The method comprises a step 260 for extracting and preprocessing a features vector to prepare the classification step. The process aims at normalizing data and reducing the dimension of the problem. The input data include all model outputs (Cf. FIG. 3) and the output data is a vector with a reduced number of dimensions. In an embodiment, the reduction of the problem dimension can be solved using either a Principal Component Analysis, a Linear Discriminant Analysis or a K-nearest neighbor algorithm.

The method comprises a step 270 to qualify the current state of an entity. In accordance with the definition of an entity proposed earlier, the classification of an entity may apply to the whole network, a single arc, a single node or a subset of the nodes and arcs of the network. In a number of embodiments of the invention, the subset of nodes and arcs of the network that form the entity are chosen so as to form a coherent set. For example, an entity may be a subset of an area that delivers water to a neighborhood, with a single input and a single output arc for the whole entity.

Various machine learning techniques can be used depending on the availability and amount of historical labeled data, composed of features vectors. In a number of embodiments, these techniques include outlier detection, clustering and classification. In a number of embodiments, the rules of machine learning are based on machine learning algorithms 271 previously trained on historical labeled features vectors. For example in the case of sufficiently available historical labeled classes, classification algorithms can analyze available historical classes and corresponding features vectors in order to build a classifier to automatically determine rules of classification of entities. A new vector of features can then be automatically classified into the relevant current class, therefore characterizing the current state and giving valuable information to an operator. For example the classification may be based on Support Vector Machine, Random Forest; Logistic Regression . . . . In a number of embodiments, classification with two classes (normal/abnormal state) can be used. In a number of embodiments classifications may also consist in types of anomalies (pressure, high/low consumption, and water quality), etc. The classification can also include an index of confidence, which indicates the certainty of the classification of the anomaly. In a number of embodiments, training of the machine learning algorithm can be triggered at any time depending on time basis (defined frequency), on performance criteria or on evolution in the dataset used.

In the case of labeled historical classes and corresponding features vectors which are insufficient, clustering or outlier detection can be used. Clustering may include techniques such as K-means or hierarchical clustering. Clustering uses past states, represented by past features vectors but without known labels. In one embodiment of the invention, the state is then declared as abnormal if not present in bigger clusters (a criterion of the size of clusters is tested).

The method comprises a step 280 to determine whether the class computed for an entity corresponds to an abnormal state ("event") according to the output of machine learning algorithms or if one of the states is detected as outlier. If an event is detected, the method goes to step 290. If the states are qualified as normal, the method goes to step 291.

The method comprises a step 290 to display structured information to the operator. A list of prioritized entities in abnormal state can then be presented to an operator in order to launch proper maintenance operations to the entities with the highest likeliness of anomaly. These entities with abnormal state are presented with additional information collected all along the previous steps (based on information contained in the model outputs and the features vector). In one embodiment, the information contains indications about quantification of the level of abnormality (for instance the value of flow of a leak, the value of head loss), time and duration of the abnormality, known location and spread of the abnormality etc. Taking into account the context settings, this information is used to prioritize the abnormal states and provide a degree of abnormality to the user.

The method comprises a step 291 to enrich an historical database of vectors of features labeled as "normal". These vectors of features are used as inputs for the learning process of algorithms. This advantageously allows having a richer database over time, and thus a more reliable prediction of normal or abnormal states.

The method comprises a step 292 to enrich historical database of vectors of features not labeled as "normal" by the method. The method comprises then a step of validation of events by the operators. In one embodiment, the operators can then input in the method, for each entity, if they confirm the event and its class. The vectors can then be labeled according to the class they belong (leak, pressure anomaly, water quality anomaly . . . ). The historical database of vectors of features is enriched with the new classified vector of features whatever the state is "abnormal" or "normal". These vectors of features are used as inputs in the learning process of algorithms. If not labeled by the operator, the vectors are still stored but without specific label. They can then be used in unsupervised or semi-supervised modes (clustering and outliers detection).

FIG. 3 displays an example of a method for identifying parameters for a target event in the prior art.

The method 250 comprises a step 310 of setting the problem according to one of the targeted events and specific entities chosen in step 240. The step aims at defining the sets of parameters corresponding to the type of targeted event for the entity. A set of parameters is defined per each target of event and entity. In a number of embodiments of the invention an event type is associated with a list of parameters, and the set of parameters is retrieved according to the event that is targeted. For example an event may be a false opening state of a valve which may be known to be characterized by inconsistent values of control variables representative of roughness and friction, while other type of events may be leaks which may be known to be characterized by abnormal values of water demand.

The method 250 further comprises a step 320 of using the hydraulic model to calculate predicted values of a set of state variables characterizing entities, at least velocity at the arcs and pressure at the nodes at second time references. This step consists in calculating a predicted value of state variables of the entity (network, its subsets, . . . ), at the second time references. The second time references can be chosen by the user independently of the first time references. For example, the second time references are separated by a predefined and constant interval (i.e. predicted values are calculated every 1 min, 5 min, or any other duration) and are not necessarily synchronized with the first time references. Methods for using a hydraulic model to calculate predicted values of the state variables of a hydraulic network are well known by people skilled in the art of water system engineering. They typically consist in, starting from the tank state at a time reference and the values of control variables, using the physical law of hydraulics for computing values of all state variables at the same time reference, and then computing values of the tank state at the next time reference. It is then possible to calculate predicted values of the state variables at all time references starting from initial values of the state variables and values of the control variables. Methods for calculating predicted values of state variables at a time reference are notably disclosed by O. Piller, "Modeling the behavior of a network—Hydraulic analysis and sampling procedures for parameter estimation". PhD thesis in Applied Mathematics from the Mathematics and Computer Science Doctoral School at the University of Bordeaux (PRES), 1995, 288 pages, Talence, France.

The method further comprises a step 330 of computing residue values of the subset of the state variables as a difference between predictions and observations at the second time references. In case the second time references and the first time references are not identical, values of observations can be calculated at the second time references, for example by building a continuous function of each observation at first time reference and picking values at desired second time references. Such a continuous function can be built in several ways. It may for example be built using an interpolation function or a regularization function. Several functions are adapted here, for example a Gaussian kernel convolution function. This step consists in computing differences between predicted and observed values of the state variables, for state variables for which observations are available. The observations of state variables may be either raw observations or pre-processed observations. Observed values of state variables may for example be pre-processed by smoothing, missing data imputation, etc. to clean the signal In cases where the system is correctly modeled and calibrated, and the inputs and outputs of the network are correctly defined, then, if there is no actual anomaly, observations and predictions of the state variables are very close and the residue values are very close to the values of the residues at calibration of the model. Conversely, the residue values can be important, i.e. an anomaly occurs, like for example when a spatial consumption of water is wrong. The objective function is used to compute the importance of the residue values. The importance of the residue value may for example be calculated as a weighted norm, or a weighted average of the absolute value of each residue value. Weights associated with the different observations/residue can be defined according to the nature of the observation (flow, pressure . . . ), the brand and accuracy of the sensor, the time into the day, the empirical variance of the measurement. More generally, the weight can be automatically defined, or defined by a user, according to an indication of confidence of the measurement.

The method 250 further comprises a step 340 of verifying if the residue values satisfy a break criterion. This step consists in verifying if the residue values of state variables are small enough for considering that values of control variables accurately describe the behavior of the entity. The break criterion can be for instance a combination of a threshold on the number of iterations, a threshold on the variation of residue values, a threshold on the gradient of the objective function with respect to the set of parameters.

When the break criterion 340 is not satisfied, the method 250 comprises a loop step 350 to change the values of the problem parameters (for instance the consumption profile) using a descent method. In an embodiment, the method can be a gradient algorithm, a conjugate gradient algorithm, a Newton algorithm, a Levenberg Marquardt algorithm, or another algorithm of the same type. This step 350 feeds a new iteration of the step 320, using the hydraulic model to calculate predicted values with modified values of problem parameters.

When the break criterion 340 is satisfied, the method 250 comprises a step 360 which is a test based on a refinement criterion. While the value of the objective function decreases, a further refinement step 370 is performed in the loop at step 320.

The method 250 further comprises a step 370 to select a subset of at least an element (node or arc). The step examines the gradient computed as the scalar product of an element (node or arc) sensitivity vector by an element contribution vector. The method discards the elements according to a selection criterion, based on sensitivity assessment. In an embodiment, those having a positive sensitivity are discarded. This step 370 feeds a new iteration of the step 320, using the hydraulic model to calculate predicted values on the selected elements.

The method 250 further comprises a step 380 to provide the outputs of the model parameters. The model outputs include the adjusted parameters, the successive values of the element sets and related objective function, and characteristics which are processed at step 260 as shown in FIG. 2. The model outputs include therefore information on various entities, from specific node or arc to subset of the network and the whole network.

Figure 4:
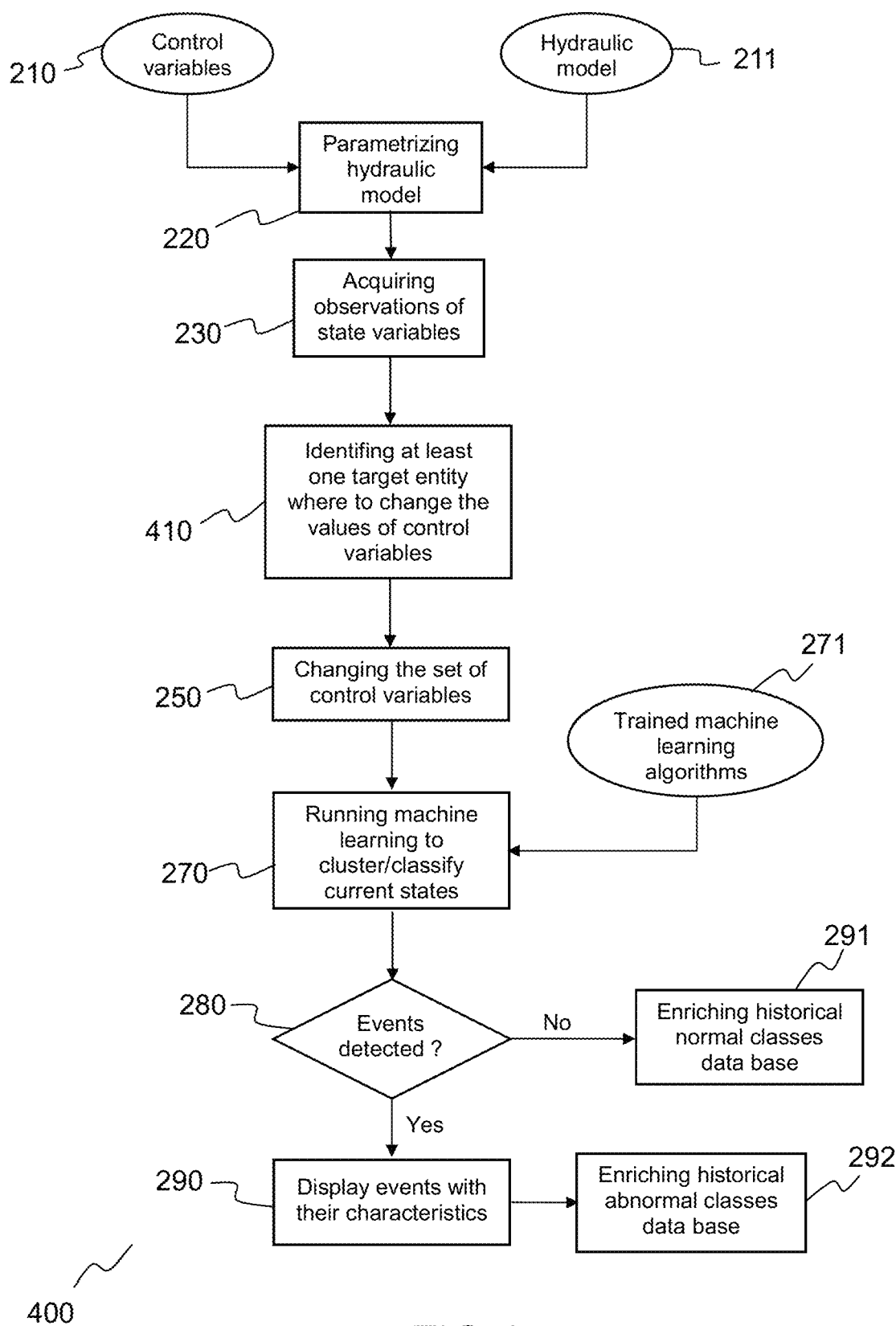
FIG. 4 displays an example of method for detecting anomalies in a water distribution system in a number of embodiments of the invention.

FIG. 4 displays an example of method for detecting anomalies in a water distribution system in a number of embodiments of the invention.

The method 400 of the invention comprises steps similar to the method 200 of the prior art, notably:
The step 220 of parametrizing a hydraulic model of the water distribution system with a set of values of control variables characterizing the network and its output at the nodes;
The step 230 of using sensors on the network to acquire observations of a subset of state variables at first time references;
The step 250 of changing the set of values of control variables using a stepwise adjustment of the control variables and a break criterion based on residue values of the state variables;
The step 270 of performing a classification of at least one entity of the network in a state according to the set of control variables.

In a number of embodiments of the invention, the method can also comprise one or more of the other steps of the method 200:
The step 280 of detecting events;
The step 290 of displaying events and their characteristics;
The step 291 of enriching the database of historical normal classes;
The step 292 of enriching the database of historical abnormal classes;
The method 400 further comprises a step 410 of identifying at least one target entity where to change the values of control variables based on at least said observations.

The aim of step 410 is to reduce the number of entities wherein the values of control variables are changed at step 250, while ensuring that, if an anomaly occurs in the water distribution system, it is found at the entities selected at step 410. Indeed, the computational load and complexity of step 250 may dramatically increase in large networks with a high number of entities.

Thus, by reducing the number of entities for which the control variables are modified, the method of the invention reduces the computational load of the detection of anomalies and produces its results faster and at least as reliably as prior art methods.

In a number of embodiments of the invention, step 410 further identifies other elements, for example the control variables to change, thus further reducing the computing cost of step 250.

In a number of embodiments of the invention, the step 250 is performed for a plurality of event types, and the step 410 identifies possible event types to test.

According to various embodiments of the invention, the identification of the entities where to change control values, of the control values to change, and of the events to test can be performed in many different ways. For example, it may rely on a statistical analysis of residue values of state variables, and a first classification of entities. It may also rely on a direct comparison of values of state variables, for example water speed, with a threshold.

More generally, in a method according to the invention, an anomaly is detected, if at least one entity is classified in a state representative of an anomaly at step 270, or if an event is detected at step 280. In a number of embodiments of the invention, some events are representative of an anomaly, while some other are not. Thus, the step 290 of displaying events and their characteristics comprises displaying an anomaly to an operator, if at least one entity has been classified in an abnormal state. In other embodiments of the invention, it is also possible to display or log, in addition to events, the classifications in a normal state. These display or log of normal states can thus be verified by an expert in order to ensure that the classification is done correctly, and that no misclassification leads to missing an anomaly.

Examples of embodiments of the invention will be presented, by way of non limitative examples, in the rest of the description.

Figure 5:
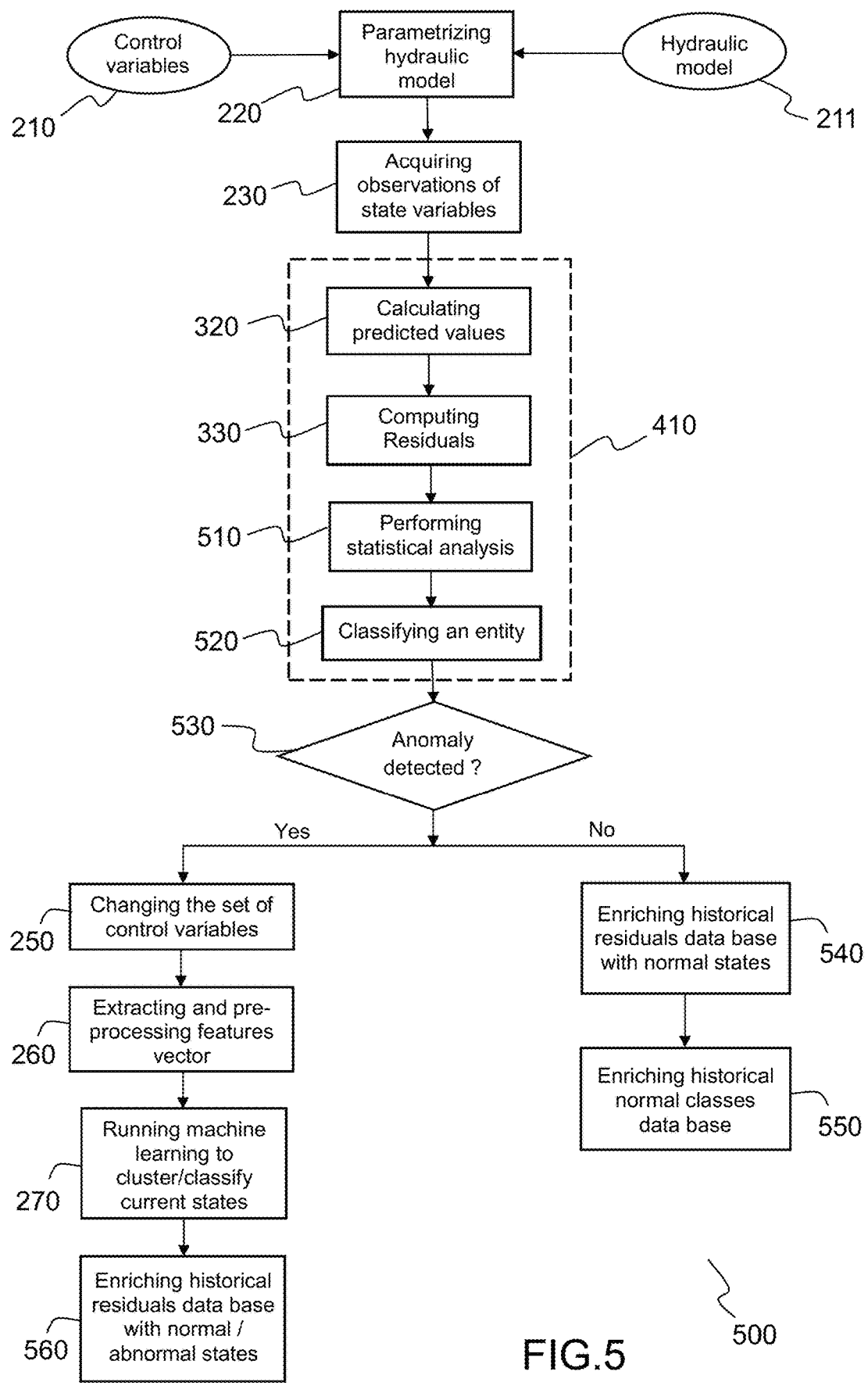
FIG. 5 displays an example of method for detecting anomalies in a water distribution system in a number of embodiments of the invention, in which the execution of stepwise iterative adjustment of properties and control variables of a hydraulic model combined to a machine learning for identifying the anomaly is dependent on the output of a classification of anomalies using a computation of residue values of state variables.

FIG. 5 displays an example of method for detecting anomalies in a water distribution system in a number of embodiments of the invention, in which the execution of stepwise iterative adjustment of properties and control variables of a hydraulic model combined to a machine learning for identifying the anomaly is dependent on the output of a classification of anomalies using a computation of residue values of state variables.

The method 500 comprises the steps 220, 230, 250, 260 and 270 of method 400. In a number of embodiments of the invention, it may also comprise at least one of the steps 280, 290, 291, 292 of the method 400.

In this example of embodiments, the step 410 of identifying at least one target entity where to change the values of control variables is performed using a statistical analysis of residue values of state variables. Using this combination enables both configuring the iterative part directly on a pre-identified class of anomaly with a pre-identified entity, and focusing on major anomalies so that the detection process is more accurate and can more easily be used by operators. Major anomalies are then those resulting in statistical discrepancies between model results and measured data, which are detected through residue analysis. The iterative process then confirms the presence of an anomaly and brings more detailed information. It may then be launched less frequently and with a lesser number of parallel instances, saving computation time.

The step 410 of identification of at least one target thus comprises the step 320 of calculating predicted values, and the step 330 of computing residues, which are known from the prior art. The residue values can be computed for all or a part of the state variables for which an observation is available.

The step 410 further comprises a step 510 of performing a plurality of statistical analyses of residue values for at least an entity for a selection of time references. This step consists in analyzing the distribution of residue values for an entity at each time reference in a time window. According to various embodiments of the invention, the time window may cover the totality or a subset of time references.

Through the plurality of statistical analyses, an anomaly can be detected if residue values are not consistent with historical observations of residue values. The use of historical distribution of residue values allows catching the usual and unusual behaviors, including variability and various properties of the residue values, to be compared with current residue values within a given time window. For example the step 510 may comprise calculating statistical inferences (n-order moment, average, standard deviation, mean or median absolute deviation, etc.) using a database of historical residue values to be compared with the corresponding statistical inferences from the current residue values. This gives more robustness to the method as it takes into account the past values and the observed behaviors.

In a number of embodiments of the invention the residue values are transformed using a Fourier transform prior to statistical analysis. In an embodiment of the invention, performing statistical analysis for an entity comprises detecting if a residue value exceeds a predefined threshold for a predefined number of successive times steps. The threshold and number of successive time steps can be predefined based on previous detections, in order to maximize the ratio of detection of anomalies when an anomaly is present (true positives), and minimize the ratio of detection of an anomaly when it does not exist (false alarms). The analysis can use statistical tests on properties of residue values, and the computation of resulting Pvalues to qualify the result of the tests. The thresholds on Pvalues can be set to obtain a level of risk of obtaining false alarms. Setting a given value then implies expecting a given percentage of false alarms, i.e. wrong reject of assumptions. In an embodiment, the statistical analysis is typically performed on residue values of pressure or velocity. For example an analysis of flow rate for detecting a leak may be performed on windows of a few hours.

The step 410 further comprises a step 520 of classifying the at least an entity of the network based on rules to be applied to the output of the statistical analysis step. Following the application of the rules, a class is given to the entities (for instance "leak", "pressure drop", "water quality issue"). In an embodiment of the invention, the rule is based on a comparison of Pvalues given by statistical tests performed in step 510, with a predefined level of risk, depending on the target level of sensitivity of the method. In an embodiment of the invention, the rule is based on a previously trained classification algorithm, enabling, based on past simulation, to analyze current vector of residue values and give the current class of the entity. In an embodiment of the invention, two classes are available, one representative of normal and the other representative of an abnormal state. In other embodiments of the invention, classes give a more accurate nature of anomaly, such as "abnormal drop of pressure", "problem with water quality" etc.

The method 500 further comprises a step 530 of determining the following step according to the current classes. If one of the classes corresponds to an abnormal state (one of the possible abnormal states) or if the state is detected as outlying, the method goes to 250. If all the classes are qualified as normal, the method goes to 540.

If one of the classes corresponds to an abnormal class, the step 250 can be adapted to the entities which have been classified as abnormal. In a number of embodiments of the invention, only control variables of the entities classified as abnormal can be initially modified at step 250. In other embodiments of the invention, control variables of the entities that are classified as abnormal, as well as control variables of adjacent entities can be initially modified at step 250. It is also possible to associate a class at the output of step 520 to control variables to modify or events to test at step 250. Step 250 is therefore launched for a reduced number of possible anomalies, corresponding to the expected anomalies, on specific subsets of nodes and arcs. This better tuned and geographically focused iterative process results in a quicker and more accurate characterization of anomaly (location, intensity). The better tuning is due in particular to stronger boundary conditions set for the problems, whereas in the step 220, the hydraulic model is less constrained.

At the output of step 270, the method 500 comprises a step 560 of enriching a database of historical residues with normal/abnormal states. This step consists if associating the residues with a "normal" label if no anomaly has been identified at step 270, an "abnormal" label, or a label representative of an event, if an event has been detected at the output of step 270. This allows enriching the database which associates residue values with a normal state, an abnormal state or an event, and allows obtaining a further classification of residue values in the further executions of the method, thus improving its efficiency over time.

Step 540 consists in enriching a database of residues with normal states. Similarly to step 560, this allows improving the classification of entities at step 520 over time.

The method further comprises a step 550 enriching the historical normal class database, in case criterion 530 is not met. This step consists in running different stepwise iterative adjustments of properties and control variables of a hydraulic model, and extracting features vectors corresponding to the different types of anomalies. These vectors are then directly considered as normal class representatives, possibly with different contexts, and stored in the normal class database for further use for training the machine learning algorithm.

Example of Embodiment: Detection of an Abnormal Decrease of Residual Chlorine Concentration By way of non limitative example of the method 500, a scenario of detection of an abnormal decrease of residual chlorine concentration is be described below.

A water distribution system is equipped with sensors that measure parameter representative of the quality of water, in addition to hydraulic sensors. It notably comprises sensors of the residual chlorine concentration (referred to as RCC below).

A hydraulic model of the network has been calibrated during a training phase, as well as a model of the evolution of the RCC. In this example, the predicted, observed and residue values are values of the RCC. During a training phase, a learning module is applied to residue values of the RCC, in order to determine the parameters of residue values representative of a normal RCC.

Once residue values of RCC are calculated, the statistical analysis compares values which are characteristic of the distribution of residue values to historical values used during the training phase. If residue values having at least one distribution property has an abnormal value, an absolute value above a threshold, for a large number of successive times of reference, a subset of the network is pre-classified in a class "abnormal diminution of RCC" with an index of confidence.

The stepwise iterative adjustment of properties and control variables of a hydraulic model is then launched with the specific subset of the network and settings corresponding to water quality anomaly, in particular the evolution of the RCC. Properties and control variables include here specific parameters of the chlorine model such as the kinetic constants for bulk water at the various sources, and the kinetic constants for each pipe material.

If no case of abnormal distribution of RCC were previously encountered in the network, the processing of results at the output of the inverse model solving can be performed using a detection of outliers or a clustering applied on the kinetic constants. When using the outlier detection, the state is compared to historical states. It is declared as outlier if the distance is above a threshold. At least a value is then classified in a class "abnormal diminution of RCC" with an index of confidence.

Information about the anomaly and its localization can then be presented to an operator through a graphical interface. This embodiment is advantageous, since it provides additional robustness to the detection of anomalies. Indeed an anomaly will be detected if raised first by the analysis of residues and then confirmed and located thanks to the inverse model, which has been more specifically tuned.

Figure 6:
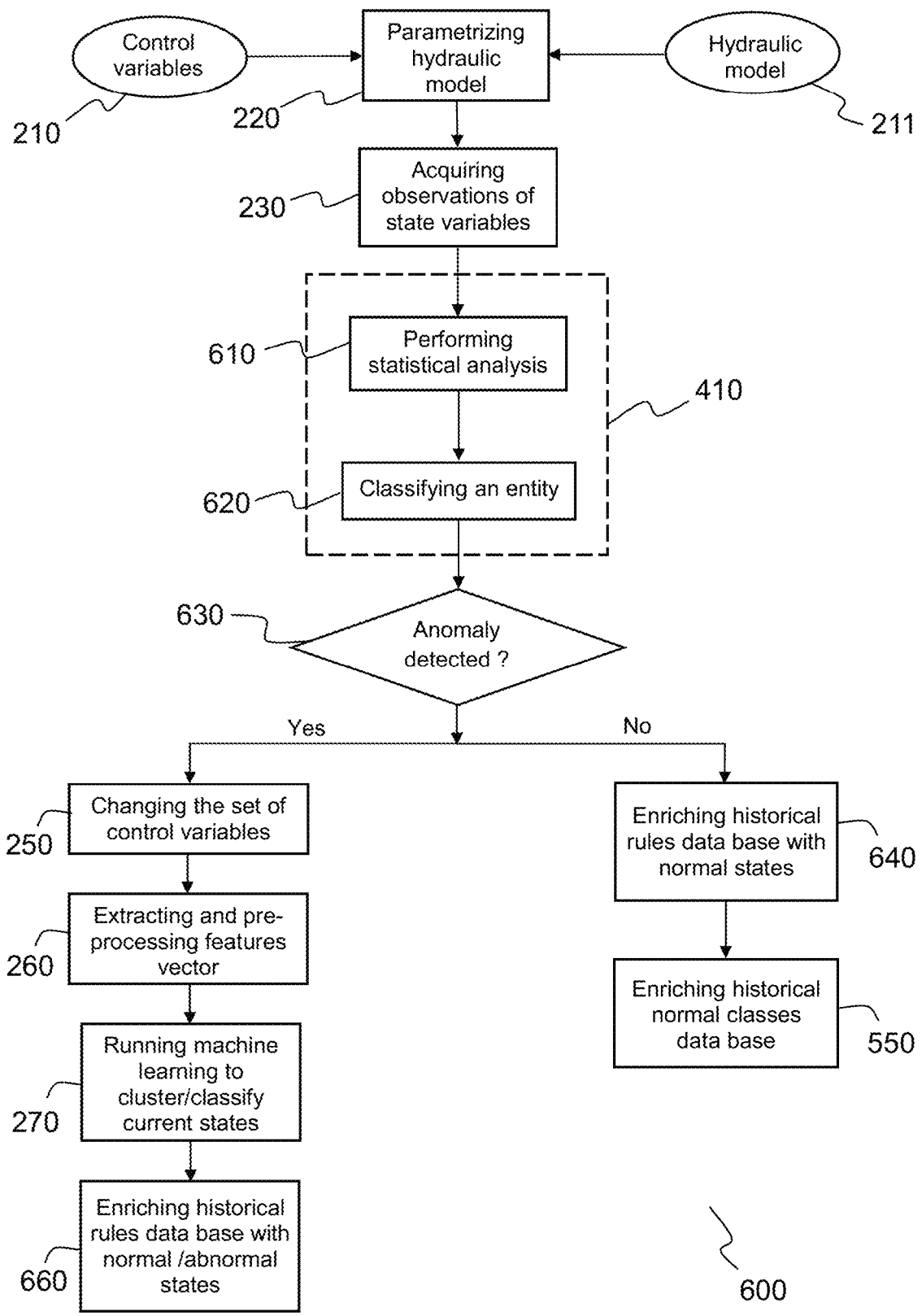
FIG. 6 displays an example of method for detecting anomalies in a water distribution system in a number of embodiments of the invention, in which the execution of stepwise iterative adjustment of properties and control variables of a hydraulic model combined to a machine learning for identifying the anomaly is dependent on the output of a classification of anomalies using a combination of rules applied to state variables.

FIG. 6 displays an example of method for detecting anomalies in a water distribution system in a number of embodiments of the invention, wherein the execution of a stepwise iterative adjustment of properties and control variables of a hydraulic model combined to a machine learning for identifying the anomaly is dependent on the output of a classification of anomalies using a combination of rules applied to state variables.

The method 600 comprises steps 220, 230, 250, 260 and 270 of method 400. In a number of embodiments of the invention, it may also comprise at least one of the steps 280, 290, 291, 292 of the method 400.

In a number of embodiments of the invention, the step 410 of the method 600 comprises a step 610 of performing a number of tests on observations in accordance with a combination of rules, without using a hydraulic model, and the step 620 of classifying a node, based on the output of step 610.

At step 610 the observations of state variables are tested to determine if there are anomalies and where, before parametrizing the iterative process. Several tests are performed, and their results are combined using rules for classifying entities into the different predefined states which have been predefined. In one embodiment, the method compares all the measured values of the variables to predefined thresholds which have been defined based on the operators' experience. If a value of a variable exceeds the threshold, corresponding anomalies are selected on an area which is predefined based on the locations of the different sensors'. In another embodiment, an anomaly is detected if the number of time steps of observation exceeds a given threshold. In an embodiment, the number of exceeding-threshold time steps to raise the anomaly is given through binomial probability computing, and a given level of risk. In another embodiment new variables are built on the basis of observations, to describe particular aspects that could be subject to anomalies. In one embodiment, the slope of linear regression over time can be computed and compared to thresholds for detecting an abnormal evolution. In another embodiment, a certain percentile can be computed on observations (for instance 5%, or 50%) and compared to predefined thresholds. In another embodiment, the thresholds can be computed based on linear combination of mean values and past observed standard deviations of the observations to take into account the usual variability of the signals. In one embodiment the different thresholds can be typically based on 2 and 3 standard deviations around the mean values.

In one embodiment each test result can be scored and the scores can be combined with a multilinear combination. The scores can be just 0 and 1, but also more accurate, to reflect different levels of suspicion, for instance linked with different levels of risk (with Pvalues) or different thresholds. The combination of scores therefore provides an index indicative of the possibility of an entity to be in an abnormal state, thus increasing the robustness. In one embodiment, the combination can make use of weights, which can be tuned in learning phases, to give more importance to a particular test. In one embodiment, one of the tests can be more reliable, but others can be gathered to become more reliable together. This combination also applies to results of tests between several entities. In one embodiment, the combination is used to assess if the abnormal behavior is similar on many entities, therefore being the results of a common driver and not a real anomaly. This combination aims at increasing the robustness of the initialization of the iterative process. Using this method, a wide variety of rules can be tested, in a number of different variables. As explained below, the relevant variables and rules can be identified, tailored and improved for a given network at steps 540, 550 and 560. In one embodiment, the tests to be applied, the rules and the combination of scores are applied differently on groups of areas. These groups of areas can be defined by the user, or by a clustering process based on historical data.

The step 410 of method 600 further comprises a step 620 of classifying an entity which is very similar to the step 520 of the method 500, except that it applies to the output of the combination of rules 610, instead of the output of statistics on residue values 510. Similarly to step 520, the step 620 can be trained using a machine learning algorithm, or tailored specifically to classify the entities according to the output of step 610. Similarly, the method 600 comprises a step 630 to detect or not an anomaly, which is very similar to the step 530 of the method 500, except that it applies to the output of step 620.

Step 250 is therefore launched with a reduced number of configuration, corresponding to the expected anomalies, on specific subsets of nodes and arcs. This better tuned and geographically focused iterative process results in a quicker and more accurate characterization of anomaly (location, intensity). The better tuning is due in particular to stronger boundary conditions set for the problems, whereas in the step 220, the hydraulic model is less constrained.

In a number of embodiments of the invention, the method 600 further comprises the step 640 of enriching the historical database of rules with normal states, and the step 660 of enriching the historical database of rules with normal and abnormal states. These steps are very similar to steps 540 and 560 respectively, instead that a database of association of rules and normal/abnormal states is enriched, instead of a database of rules of association of residue values with normal/abnormal states. This enrichment permit, over several executions of the method, to train the rules of pre-detection of anomalies to a given water distribution network. Thus, even without a priori knowledge of rules on the state variables which are representative or not of an abnormal state, the method is able to automatically adapt to the network, and adopt the most relevant rules. In a number of embodiments of the invention, the system is initialized with arbitrary rules: for example, the 1% of nodes having the most important water flow will be classified as abnormal. The execution of step 250 permits to determine those which are actually in an abnormal state, and the step 660 can enrich the database with the knowledge of the node which were in an actual normal or abnormal state. Over several execution of the method the rules and classification at step 610 and 620 acquire sufficient knowledge of past events to switch from arbitrary to tailored rules of pre-detection of events. In a number of embodiments of the invention, the method 600 also comprises the step 550 of the method 500.

Example of Embodiment: Detection of an Abnormal Increase of Water Demand Using a Pre-Detection Based on a Combination of Rules By way of non-limitative example of the method 600, a scenario of detection of an abnormal increase of water demand is now described below.

This example demonstrates the ability of a method 600 according to the invention to detect an abnormal increase of water demand, possibly linked to a leak, with a pre-detection based on a combination of rules.

This example describes the detection of an abnormal increase of water demand, which can be linked to a leak. The observed time series of flow rates are combined to form water demands for given areas. Different percentiles are computed on these new time series and compared to thresholds based on linear combinations of past observed standard deviations. Based on previous executions of the method a limit number of successive time steps for which the percentiles needs to be above the threshold to pre-detect an anomaly has been learnt. Using machine learning this limit number of successive time steps is calculated as an optimal number to avoid missing possible anomalies, and not to have too many pre-detections. Let's assume that for 3 given areas, the percentiles are above the thresholds at more time steps than the limit number of time steps which was learnt for each given area. For all other areas the percentiles are below the thresholds at the required number of time steps. For them, the given score is 0. For each of the 3 areas triggering the thresholds, a score of 1 is given and the rule of combination then applies: For each area, if its own score is 1, the percentage of other areas with a score equal to 0 is compared to a predefined threshold. In the current case, this percentage is above the threshold for the 3 areas as many other areas have a score of 0. The 3 areas are therefore pre-detected as abnormal. Pre-detecting anomalies in 3 areas instead of one prevents a false alarm based on possible changes of water demand occurring at the same time in many areas. These possible changes can be due to seasonality or a specific common event that is not meant to be brought to the attention of the operators. This increases the robustness of the method by decreasing the rate of false alarms.

The stepwise iterative adjustment of properties and control variables of a hydraulic model is then launched with the specific subset of these 3 areas of the network and settings corresponding to water demand increase. Properties and control variables are set to detect leaks in the 3 given areas, as subsets of nodes where abnormal demand is allocated (their number decreasing through iteration process), and their water consumption time profiles.

Information about the anomalies and their localizations can then be presented to an operator through a graphical interface. This embodiment is advantageous, since it provides additional robustness to the detection of anomalies. Indeed an anomaly will be detected if raised by first a combination of rules on observations and confirmed through the inverse model, more specifically tuned.

Figure 7:
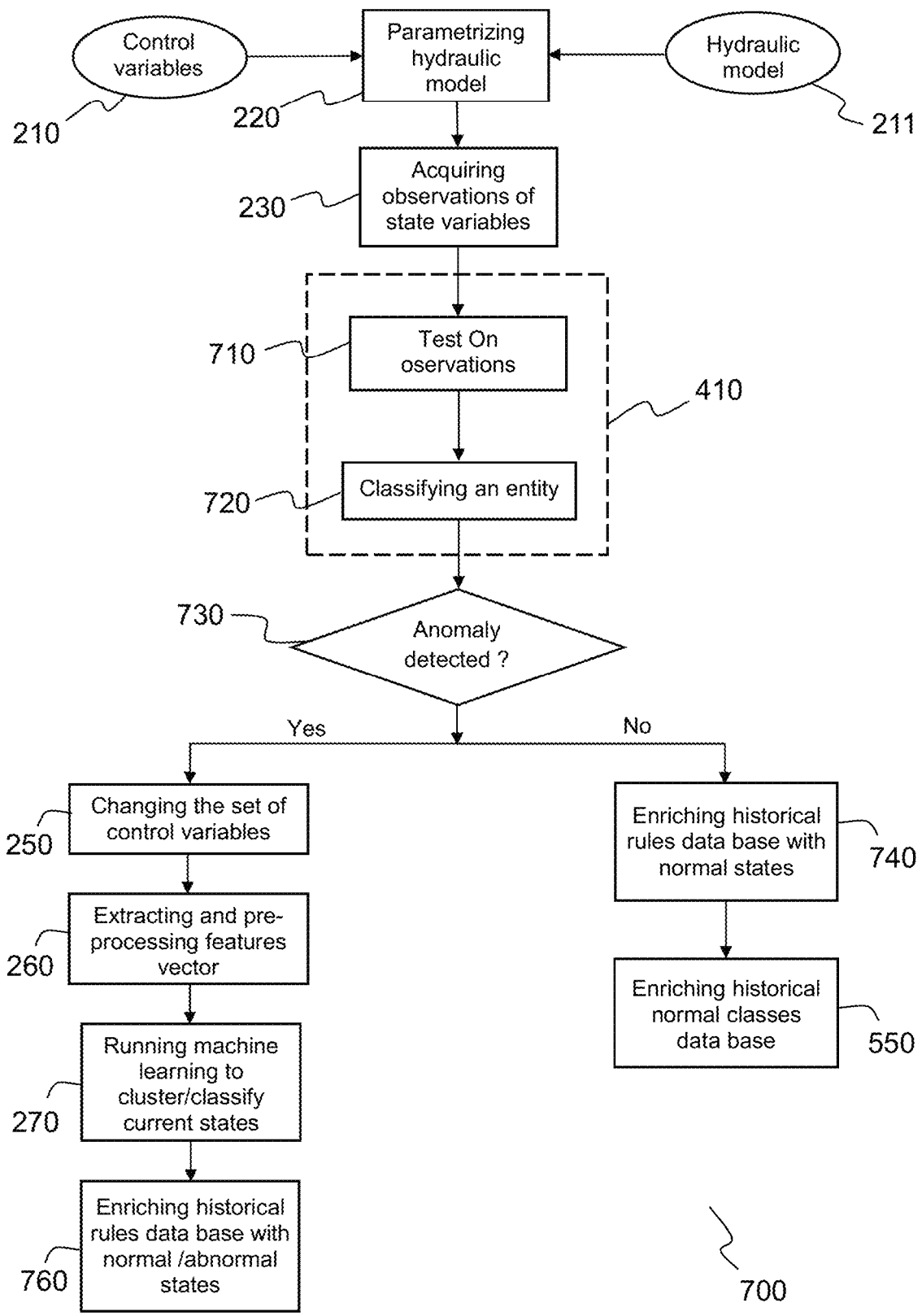
FIG. 7 displays an example of method for detecting anomalies in a water distribution system in a number of embodiments of the invention, using statistical learning for pre-detecting and pre-characterizing an anomaly FIG. 8 displays an example of a presentation of the localization of anomalies to an operator.

FIG. 7 displays an example of a method for detecting anomalies in a water distribution system in a number of embodiments of the invention, using statistical learning for pre-detecting and pre-characterizing an anomaly and the use of a stepwise iterative adjustment of properties and control variables of a hydraulic model, added to machine learning for identifying the anomaly. The way of using this combination enables both configuring the iterative part directly on a pre-identified class of anomaly, with a pre-identified entity, and focusing on major anomalies to make the detection process more accurate and easily usable by operators. The iterative process then confirms the presence of an anomaly and brings more detailed information.

The method 700 comprises the steps 220, 230, 250, 260 and 270 of method 400. In a number of embodiments of the invention, it may also comprise at least one of the steps 280, 290, 291, 292 of the method 400.

In a number of embodiments of the invention, step 410 of the method 600 comprises a step 710 of performing a number of tests on observations in accordance with a combination of rules, without using a hydraulic model, and a step 720 of classifying a node, based on the output of step 710.

At step 710, the observations of state variables are tested to determine if there are anomalies and where, before parametrizing the iterative process. The method simulates the expected values of observations, based on their past values and additional drivers. In a number of embodiments of the invention, several models are trained on past data, and the model that yields the best prediction of past data is selected. In one embodiment, the method contains models based on time-series analysis such as autoregressive moving average (ARMA) technique, or seasonal auto-regressive integrated moving average technique (SARIMA). The ARMA and SARIMA models are notably disclosed by Box, George; Jenkins, Gwilym (1970). Time Series Analysis: Forecasting and Control. San Francisco: Holden-Day. In one embodiment, the method contains models based on machine learning algorithm such as random forest or artificial neural networks. In one embodiment, the method includes models using past or current values from other variables for a given observation of variable. The additional drivers are variables or parameters that influence the observations. In one embodiment, the temperature and rainfall volumes are included. In another embodiment, the calendar and periods of time with specific events are included. The simulated values for observations are then compared to actual observations through residue values computing. The residue values are tested with different tests and their results are combined through rules for classifying entities into the different predefined states. In one embodiment, the method tests all the residue values by comparison to predefined thresholds based on experience of operators. If residue values exceed the thresholds, corresponding anomalies are selected in an area which is defined based on the locations of the different sensors. In another embodiment, the anomalies are flagged if too many time steps of residue values are exceeding a given threshold, for a given time window. This time window depends on the nature of variables and anomalies to be detected. In one embodiment, the length of time window can be 6 hours. In an embodiment the number of exceeding-threshold time steps to raise the anomaly is given through binomial probability computing, and a given level of risk. In another embodiment new variables are built on the basis of residue values, to describe particular aspects that could be subject to anomalies. In an embodiment, the cumulated sum of residue values over time may be computed and compared to thresholds for detecting an abnormal evolution. In another embodiment, the distribution of residue values is tested with a statistical method, to be compared to past distribution of residues.

If a test reveals a significant change in distribution, an anomaly can be flagged. In another embodiment, the thresholds can be computed based on past observed standard deviations of the observations to take into account the usual variability of the signals. In one embodiment, the numbers of standard deviations to be used can be typically 2 and 3. In an embodiment each test result can be scored and the scores can be combined with a multi-linear combination. The scores can be just 0 and 1, but also more accurate, to reflect different levels of suspicion, for instance linked with different levels of risk (with Pvalues) or different thresholds. The combination of scores therefore gives the general suspicion level on each entity, increasing the robustness. In one embodiment, the combination can make use of weights, which can be tuned in learning phases, to give more importance to a particular test. In one embodiments, one of the test can be more reliable, but others can be gathered to become more reliable together. This combination also applies to results of tests between several entities. In one embodiment, the combination is used to assess if the abnormal behavior is similar on many entities, therefore being the results of a common driver and not a real anomaly. This combination aims at increasing the robustness of the initialization of the iterative process. The machine learning algorithms allow learning which state variables, on which entity, are representative of an anomaly in a given network. More generally, reliability of results of tests can be improved using learning methods which associate thresholds on observations to the presence or absence of an anomaly; the principle of adaptation of threshold is similar to the adaptation of rules, except that it is applied directly on thresholds of observations, instead of being applied to rules.

The step 410 of the method 700 further comprises a step 720 of classifying an entity which is very similar to step 520 of the method 500, except that it applies to the output of the tests of step 710, instead of the output of statistics on residue values 510. Similarly to step 520, step 720 can be trained with a machine learning algorithm, or tailored specifically to classify the entities according to the output of step 710. Similarly, the method 600 comprises a step 730 to detect or not an anomaly, which is very similar to step 530 of the method 500, except that it applies to the output of step 720.

Step 250 is therefore launched with a reduced number of pre-detected anomalies, corresponding to the expected anomalies, on specific subsets of nodes and arcs. This better tuned and geographically focused iterative process results in a quicker and more accurate characterization of anomaly (location, intensity). The better tuning is due in particular to stronger boundary conditions set for the problems, whereas at the step 220, the hydraulic model is less constrained.

In a number of embodiments of the invention, the method 700 further comprises the step 740 of enriching the historical database of observations with normal states, and step 760 of enriching the historical database of observations with normal and abnormal states. These steps are very similar to steps 540 and 560 respectively, save for the fact that a database of association of observations and normal/abnormal states is enriched, instead of a database of observations of association of residue values with normal/abnormal states. In a number of embodiments of the invention, the method 600 also comprises step 550 of the method 500. Thus, after several executions of the method, machine learning algorithms allow identifying the state variables, entities and thresholds which are representative of an anomaly.

Example of Embodiment: Detection of an
Abnormal Increase of Water Demand Using a
Pre-Detection Based on Thresholds on
Observations By means of non-limitative example of the method 700, a scenario of detection of an abnormal increase of water demand is described below.

Similarly to the previous example, this example demonstrates the ability of a method according to the invention to detect an abnormal increase of water demand, possibly linked to a leak. However, this example, based on the method 700, uses a direct comparison of observations with thresholds rather than a combination of rules.

This example describes the detection of an abnormal increase of water demand, which can be linked to a leak. The observed flow rates are combined to form water demands for given areas. These water demand are simulated with the use of past water demands and time series analysis. The simulated variables are used to compute residue values with observations. The cumulated sums of residue values are computed. They are compared to thresholds. These thresholds are based on observed variabilities of the cumulated sums of residue values in the past. It means that they use measurement of the variabilities, here based on computed means and standard deviations. In this example, for 2 areas over the whole network, the cumulated sum of residue values exceeds the given thresholds. This means that the expected behavior in terms of water demand is not observed on these 2 areas, as residue values are big enough, on a sufficient number of time steps, to say there is a statistical deviation. A pre-detection of abnormal water demand increase is raised on them.

The stepwise iterative adjustment of properties and control variables of a hydraulic model is then launched with the specific subset of the network and settings corresponding to water demand increase. Properties and control variables are set to detect leaks on the 2 given areas, as subsets of nodes where abnormal demand is allocated (their number decreasing through iteration process), and their water consumption time profiles.

Information about the anomalies and their localizations can then be presented to an operator through a graphical interface. This embodiment is advantageous, since it provides additional robustness to the detection of anomalies. Indeed an anomaly will be detected if raised by first a combination of rules on observations and confirmed through the inverse model, more specifically tuned.

Figure 8:
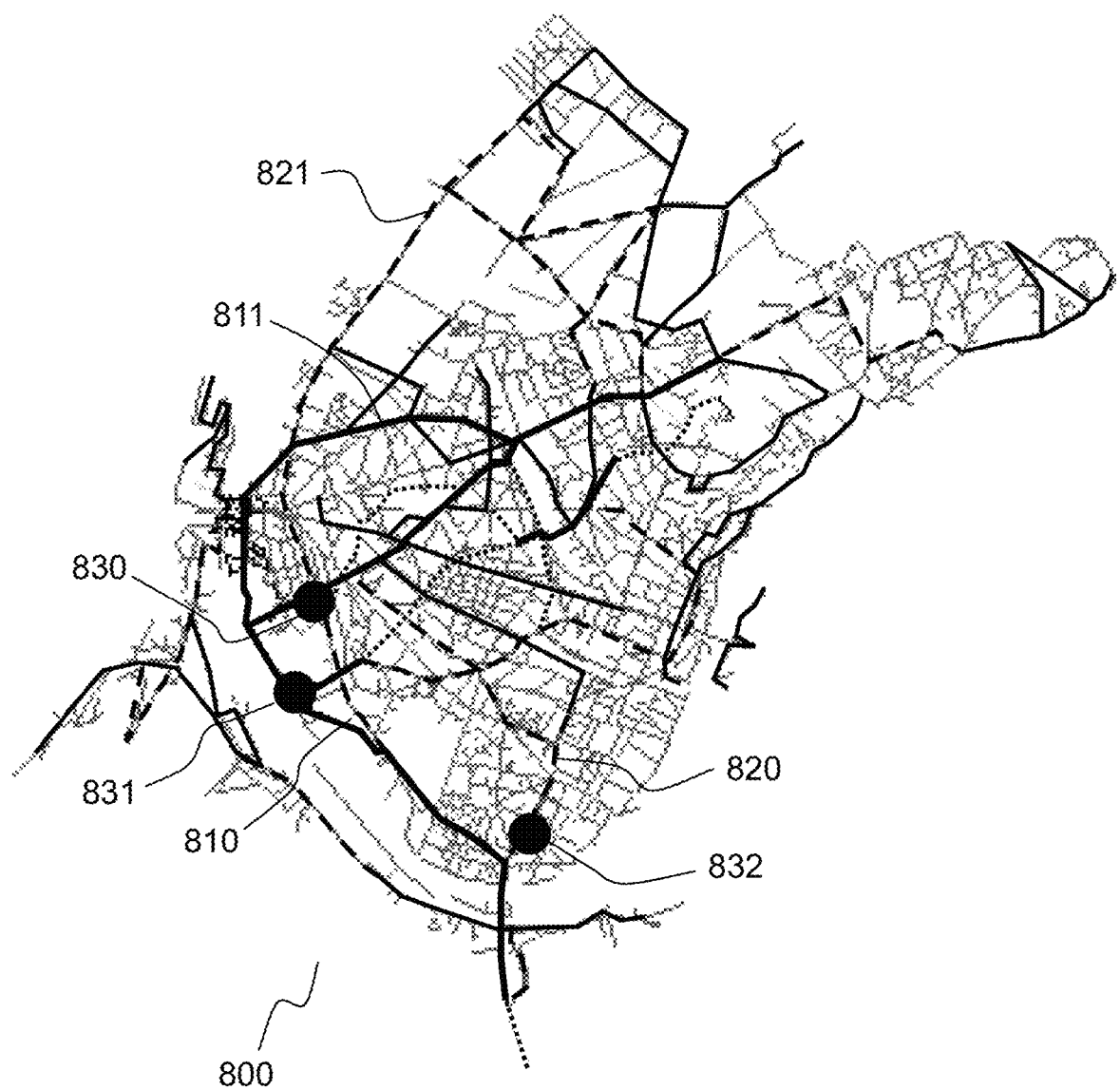

FIG. 8 displays an example of a presentation of the localization of anomalies to an operator.

A map 800 of the network of a water distribution system is displayed to an operator through a display device. The map contains lines that represent pipes of the system, the width of the lines being representative of the diameter of the pipes. The system contains large pipes, such as pipes 810 and 811, and smaller pipes, such as pipes 820 and 821. Three leaks 830, 831, 832 have been localized in the network and are represented using large circles. Information about the relative importance of the leaks can be inserted. For example, the diameter of the circles may increase with the importance of the leak. It may also be possible to represent only the leak that is considered as the most severe, or display additional information about the leak, for example a list of past leaks that had the closest characteristics.

The examples described above are given as illustrations of embodiments of the invention. They do not in any way limit the scope of the invention which is defined by the following claims.

The invention claimed is:

1. A computer implemented method for detecting anomalies in a water distribution system composed of a network comprising a plurality of nodes and a plurality of arcs and a plurality of pieces of equipment, the pieces of equipment comprising at least valves and pumps, an entity referring to a set of at least one of the plurality of nodes and/or at least one of the plurality of arcs and/or at least one of the plurality of pieces of equipment, said method comprising:
   parametrizing a hydraulic model of the water distribution system with a set of values of control variables;
   using sensors of at least water velocity and pressure on the network to acquire observations of a subset of state variables at first time references; then
   classifying at least one entity in a set of classes comprising at least one class representative of an abnormal state based on at least said observations; then
   identifying at least one target entity where to change the values of control variables, said identifying depending at least on one entity classified in said at least one class representative of an abnormal state; then
   changing the set of values of control variables of only said at least one target entity identified, using a stepwise adjustment of the control variables and a break criterion based on residue values of the state variables, wherein changing the set of values of control variables results in changing water velocity or pressure on the at least one target entity in the network; and then
   performing a classification in a class representative of an abnormal state of at least one entity of the network according to the set of control variables issued from said changing step,
   wherein changing the set of values of control variables using a stepwise adjustment of the control variables and a break criterion based on residue values of the state variables comprises:
      A) changing the set of values of the control variables;
      B) using the hydraulic model to calculate predicted values of a set of state variables comprising at least water velocity and pressure at the nodes at the time references;
      C) computing residue values of the set of state variables as a difference between predicted values and observations at the time references;
      D) if said differences satisfy a break criterion, going to step F);
      E) if not, changing the set of values of the control variables and going back to step B);
      F) if said differences do not satisfy a refinement criterion, selecting a subset of the network where to calculate predicted values, going back to step B),
   wherein identifying at least one target entity where to change the values of control variables based on at least said observations comprises:
   using the hydraulic model to calculate predicted values of a set of state variables comprising at least a water velocity and pressure at the nodes, said predicted values being associated to second time references;
   computing residue values of the subset of the state variables as a difference between predicted values and observations at the second time references;
   performing a statistical analysis of residue values at an entity of the network at a selection of the time references;
   classifying the entities of the network based on rules applied to the output of the statistical analysis.

2. The method of claim 1, further comprising identifying at least one control variable to change based on at least said observations.

3. The method of claim 1, wherein said at least one target entity is identified by being classified in an abnormal state based on the comparison of residue values and a predefined threshold.

4. The method of claim 1, wherein identifying at least one target entity where to change the values of control variables based on at least said observations comprises identifying an arc of the network wherein a value of an observation of water speed exceeds a threshold at a target entity.

5. The method of claim 1, wherein changing the set of values of control variables is performed for at least one event type, and the control variables to modify are based on said at least one event type.

6. The method of claim 5, wherein a plurality of event types is tested, and one instance of changing the set of values of control variables is performed for each event type.

7. The method of claim 1, wherein changing the set of values of control variables is performed for at least one event type, and the control variables to modify are based on said at least one event type, and wherein at least changing the set of values of control variables is performed for at least one event type chosen using classification of the entities of the network based on rules applied to the output of the statistical analysis.

8. The method of claim 1, comprising:
detecting an anomaly based on the output of identifying at least one target entity where to change the values of control variables based on at least said observations;
if no anomaly is detected, enriching a database of normal states of the entities;
if an anomaly is detected:
changing the set of values of control variables using a stepwise adjustment of the control variables and a break criterion based on residue values of the state variables;
performing the second classification of at least one entity of the network in a state according to the set of control variables.

9. The method of claim 1, wherein the refinement criterion comprises the calculation of values of one of a least square and a Bayesian objective function, and the selection and modification of control variables is determined by a Levenberg-Marquardt algorithm.

10. The method of claim 1, wherein the machine learning algorithm performing the classification of the at least one entity of the network in a state according to the set of control variables is previously trained.

11. The method of claim 1, wherein the control variables comprise scalar variables comprising the topology and the topography of the network, and time-based variables comprising the inputs and outputs of the network having at least one value at each time reference.

12. The method of claim 1, wherein state variables further comprise pressure.

13. A system for detecting anomalies in a water distribution system composed of a network of nodes, said system comprising:
sensors of at least water velocity and pressure at a subset of nodes of the network;
a computing device comprising a processor;
communication links between sensors and the computing device;
a storage media;
wherein the computing device is configured to:
retrieve an initial set of values of control variables comprising the network and its output at the nodes from the storage media and using it to parametrize a hydraulic model of the water distribution system;
use communication links between sensors on the network to acquire observations of a subset of the state variables, said observations having time references;
execute a method according to claim 1.

14. A computer program product, stored on a non-transitory computer-readable medium, for detecting anomalies in a water distribution system composed of a network of nodes, said computer program product comprising code instructions for executing a method according to claim 1.

15. The method of claim 1,
wherein changing the set of values of control variables is performed for at least one abnormal event type, and the control variables to modify are based on said at least one event type; and
wherein in said step of changing the set of values of control variables, a plurality of abnormal event types is tested, and one instance of changing the set of values of control variables is performed for each abnormal event type.

16. The method of claim 1, wherein the machine learning algorithm further comprises classifying the at least one entity by including an index of confidence indicating a certainty of the classification of the anomaly.

17. The method of claim 1, further comprising triggering the machine learning algorithm on a time basis, on a performance criteria, or on an evolution in a dataset.

* * * * *